United States Patent [19]

McFarland

[11] Patent Number: 4,579,556
[45] Date of Patent: Apr. 1, 1986

[54] ELASTICIZED BOW-SHAPED DUAL BAFFLE PAD

[75] Inventor: Timothy M. McFarland, Neenah, Wis.

[73] Assignee: Kimberly-Clark Corporation, Neenah, Wis.

[21] Appl. No.: 672,018

[22] Filed: Nov. 16, 1984

[51] Int. Cl.$^4$ .............................................. A61F 13/16
[52] U.S. Cl. ................................................ 604/385 A
[58] Field of Search ............... 604/385, 386, 387, 389, 604/358, 397, 398, 393

[56] References Cited

U.S. PATENT DOCUMENTS

| | | |
|---|---|---|
| 2,969,065 | 1/1961 | Farnsworth . |
| 4,246,900 | 1/1981 | Schroder . |
| 4,315,508 | 2/1982 | Bolick . |
| 4,324,245 | 4/1982 | Mesek et al. . |
| 4,338,938 | 7/1982 | Seavitt . |
| 4,405,310 | 9/1983 | Karami ............................. 604/389 |
| 4,405,397 | 9/1983 | Teed . |
| 4,410,324 | 10/1983 | Sabee . |
| 4,430,088 | 2/1984 | Karami . |
| 4,496,360 | 1/1985 | Joffe et al. . |

FOREIGN PATENT DOCUMENTS

| | | |
|---|---|---|
| 0091412 | 2/1983 | European Pat. Off. . |
| 0098512 | 1/1984 | European Pat. Off. . |
| 2103093 | 2/1983 | United Kingdom . |

Primary Examiner—John D. Yasko
Attorney, Agent, or Firm—Paul A. Leipold; J. J. Duggan

[57] ABSTRACT

The invention generally provides a pad that has a double system of baffles at the edges. The pad is composed of an outer impervious backing sheet, an inner absorbent layer, and a body-side permeable web. The impervious backing sheet is of greater dimensions than the absorbent and is folded over the permeable web and absorbent layer and fastened to the permeable web. Further, at least a portion of the folded-over portion is elasticized at a distance spaced from the absorbent material such that when the elastic contracts, the pad bows with the elasticized fold raising above the surface of the pad to form a baffle. This results in a dual baffle structure wherein the lower baffle is formed over the absorbent and also an upstanding baffle containing the elastic is formed that extends above the surface of the pad.

11 Claims, 9 Drawing Figures

ELASTICIZED BOW-SHAPED DUAL BAFFLE PAD

TECHNICAL FIELD

This invention relates to disposable absorbent pads. It particularly relates to disposable incontinence pads and catamenial pads.

BACKGROUND

Disposable absorbent articles are well known and have many uses. For example, disposable diapers are intended to absorb and contain urine; bandages are intended to absorb and contain blood and other body exudates; while cantamenial pads are intended to absorb and retain menstrual fluids. In each instance, the disposable absorbent article absorbs and retains a liquid, thereby preventing that liquid from soiling, wetting, or otherwise contaminating the vicinity surrounding the point of liquid discharge. For example, U.S. Pat. No. Re. 26.151 which issued on Jan. 31, 1967 to R. C. Duncan et al. entitled "Disposable Diaper" teaches a disposable diaper intended to absorb urine and prevent the wetting of the wearer's clothing.

Disposable absorbent articles should perform without leaking and several concepts have been proposed to improve the liquid containment characteristics of disposable absorbent articles such as disposable diapers. U.S. Pat. No. 3,999,548 entitled "Disposable Diaper Having Fluid Trap" which issued to J. Hernandez on Dec. 28, 1976 teaches that the liquid containment characteristics of a diaper can be improved by securing sealing strips of waterproof material to the face sheet of the diaper. Alternatively, U.S. Pat. No. 3,860,003 entitled "Contractible Side Portions For a Disposable Diaper" which issued to K. B. Buell on Jan. 14, 1975 and U.S. Pat. No. 4,050,462 entitled "Disposable Diaper With Elastically Constricted Crotch Section" which issued to L. S. Woon et al. on Sept. 7, 1977 both teach a concept for reducing liquid leakage which involves providing an elastic member in a disposable diaper. The elastic member is positioned so that when the diaper is worn, the diaper is drawn snugly about the legs of the wearer. The elastic causes the diaper to form a seal about the leg of the wearer thereby preventing liquid from leaking out of the diaper.

While diaper formation techniques are well developed, the formation of pads for incontinence uses has not resulted in as effective a garment. The shaping techniques of diaper formation have not produced effective incontinence garments. The adult body is shaped differently and has different liquid capacity requirements and fit problems than the infant.

Many articles used as incontinent products for mild incontinence or for menstrual pads have been found unsatisfactory as they are bulky and/or ineffective. Many such garments are formed by forming flat sheets into a diaper-like structure for incontinent use. Other pads for catamenial use have been formed in thin flat structures, but these structures have been low in absorption. Further, flat structures have a tendency to wrinkle between the legs during use causing discomfort and distorting the target area where the exudate will be located causing leakage.

Small elasticized pads have been proposed, such as in U.S. Pat. No. 3,371,668, to Johnson in which an elasticized sanitary napkin is disclosed. The sanitary napkin has elastic threads that are imbedded in the napkin, running in the long direction of the napkin. Another small elasticized pad has been proposed in European Patent application No. 0,091,412, of Nedestam in which a sanitary napkin having elasticized edges and a raised center portion is disclosed. However, these pads have not found wide acceptance as they are bulky and do not fit the female form to provide both comfort and absorbency.

The U.K. patent application GB No. 2,103,093 of Blaney discloses a diaper structure having elasticized flaps that are adapted to fit to the legs of the diaper wearer and minimize leakage. The flaps are formed at the edges of a diaper and exert a contact pressure on the skin of the leg when the diaper is fastened in place. There has been proposed in U.S. Pat. No. 4,182,334 a perineal shield device for containment of discharge caused by incontinence. While this device has been effective, there still are leakage problems that occur. The leakage problem is particularly acute in instances where there is rapid discharge of urine that may leak from the pad prior to being absorbed.

Therefore, there remains a need for a device for reliable absorption of urine discharged by mildly incontinent persons. There is a need for such a device that is not obtrusive, low in cost, and very effective.

DISCLOSURE OF THE INVENTION

An object of the invention is to overcome disadvantages of prior incontinent and catamenial devices.

A further object of this invention is to form a pad that will not leak during rapid discharge of urine.

An additional object of this invention is to create a comfortable, nonobtrusive absorbent pad for catamenial use or for use by mildly incontinent persons.

These and other objects of the invention are generally accomplished by providing a pad that has a double system of baffles at the edges. The pad is composed of a outer impervious backing sheet, an inner absorbent layer, and a body-side permeable web. The impervious backing sheet is of greater dimensions than the absorbent and is folded over the permeable web and absorbent layer and fastened to the permeable web. Further, at least a portion of the folded-over portion is elasticized at a distance spaced from the absorbent material such that when the elastic contracts, the pad bows with the elasticized fold raising above the surface of the pad to form a baffle. This results in a dual baffle structure wherein a lower baffle is formed over the absorbent and also an upstanding baffle containing the elastic is formed that extends above the surface of the pad.

In a particularly preferred form of the invention the pad is rectangular and the elastic baffle extends substantially the entire length of both sides of the pad with the absorbent part of the pad forming a generally smooth and ungathered absorbent surface. The preferred absorbent material is a coform absorbent that has adhered thereto a permeable surface. The preferred pads further are of a size such that they cover the genital area comfortably without becoming excessively compressed while the person is wearing them.

MODES FOR CARRYING OUT THE INVENTION

The pad of the invention offers numerous advantages over the prior art pads for mild urinary incontinence and catamenial use. The pad of the invention is comfortable to wear. The pad of the invention further is low-cost in formation as it is generally rectangular and is formed of conventional materials. The pad of the invention further has the advantage that the dual baffle arrangement provides greater protection against the leakage of urine, particularly during rapid discharge when the urine may not all be immediately absorbable. The pad of the invention further is comfortable and nonobtrusive, even though having a relatively large moisture-absorption capability. These and other advantages of the pad of the invention will be apparent from the detailed description below, particularly with view to the description of the drawings.

Figure 1:
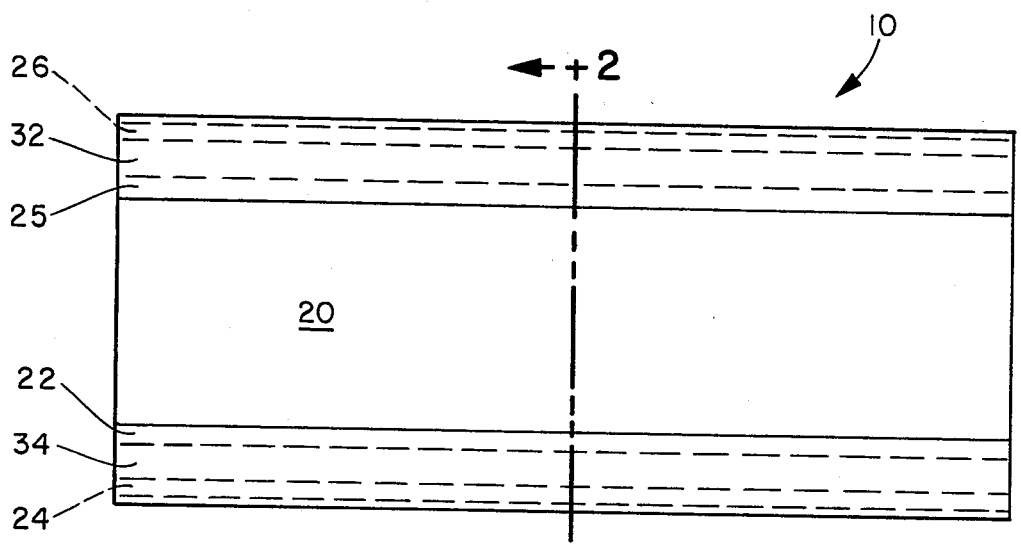
FIG. 1 is a plan view of a pad in accordance with the invention.
Figure 2:
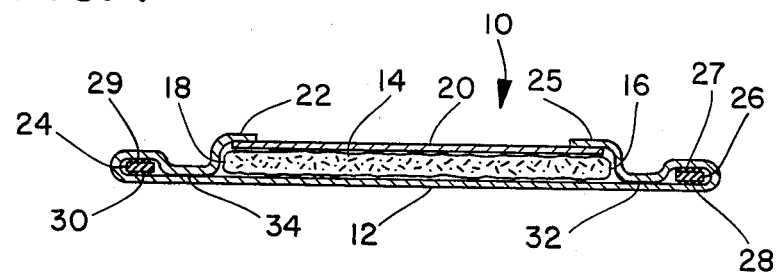
FIG. 2 is a cross-section of the pad of FIG. 1 taken on line 2—2 of FIG. 1.

FIG. 1 illustrates in plan view a pad in accordance with the invention. The pad of the invention in FIG. 1 is shown in cross-section in FIG. 2. The pad 10 is composed of a impervious backing sheet 12 that extends beyond the edges 16 and 18 of absorbent layer 14. The absorbent material is covered by a permeable web 20 to which the impervious backing sheet is attached at 22 and 24. In the folded portion beyond the edges 16 and 18 of the absorbent material the impervious backing sheet is folded over elastics 24 and 26 that are adhesively connected to the backing sheet below the elastics at 28 and 30 and above at 27 and 29. The backing sheet is further adhered to itself in the portions 32 and 34 that are located between the elastics 24 and 26 and the edges of the absorbent 16 and 18. The backing sheet 12 is adhered to the permeable web 20 and also preferably to absorbent 16 at 22 and 25. The portion outside the absorbent where the backing sheet is adhered to itself or surrounds the elastic form the upstanding baffle when the elastic contracts. The views of FIGS. 1 and 2 are with the elastics 24 and 26 in extended condition.

Figure 3:
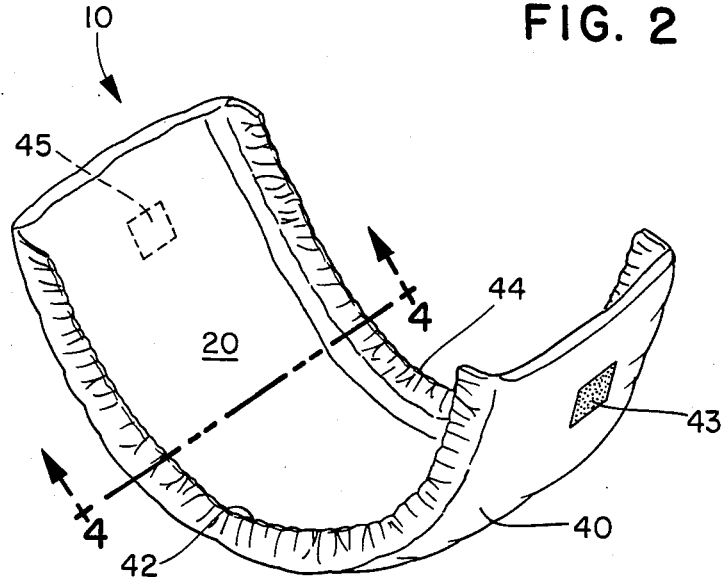
FIG. 3 is a perspective view of a pad in accordance with the invention.
Figure 4:
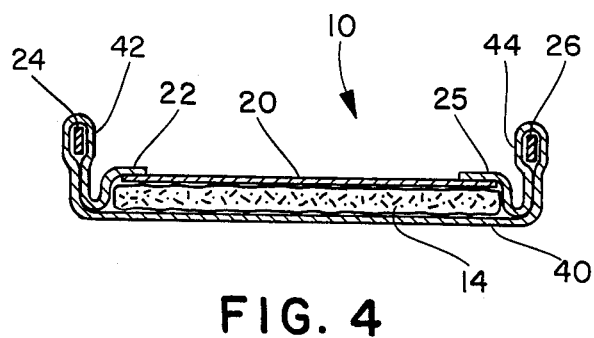
FIG. 4 is a cross-section along line 4—4 of FIG. 3.

The perspective view of FIG. 3 and cross-sectional view of FIG. 4 illustrate the pad in accordance with the invention that has been allowed to assume the shape that results when the elastics 24 and 26 relax and contract. It is noted that the bottom 40 of the pad in the preferred embodiment is generally smooth and ungathered with the upstanding baffles 42 and 44 forming a trough-like member with a generally smooth bottom 40 and vertical sides forming the upstanding baffles 42 and 44. It can be seen that the structure has baffles 22 and 24 that inhibit the movement of moisture from within or below the absorbent around the edges of the pad. The upstanding baffles 42 and 44 further inhibit motion of the liquid that is on the surface of the pad as well as they tend to seal the pad against the perineal region of the wearer.

The bowed shape of the pad in combination with the upstanding baffles 42 and 44 and lower baffles 22 and 24 are believed to result in the superior fit and leak-resistance of the instant pad. Further, the elastics 24 and 26 not being under significant tension when the garment is worn allow easy deformation of the edges of the garment to conform with bodily shape or adjust for movement.

Figure 5:
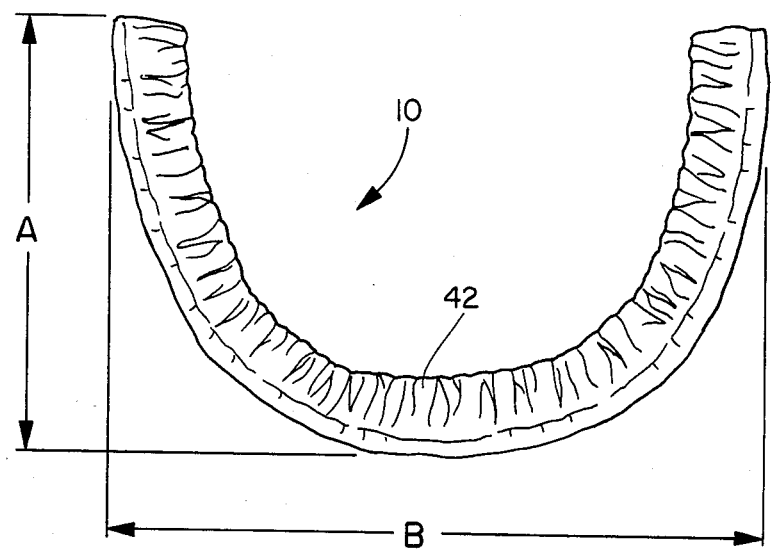
FIG. 5 is a view showing the height and length relationship of the pad of the invention.

The illustration of FIG. 5 shows the bowed pad of the invention in relaxed state. The bowed height of the pad is indicated as "A." The bowed length is indicated as "B." The bowed height "A" of the pad of the invention is typically between about 0.5 and about 5 inches in height. A preferred range of "A" is between about 2.5 and about 3.5 inches for fit of the typical woman. The bowed length "B" may be typically between about 6.5 and about 12 inches. The preferred bowed length is about 7.5 to about 8 inches to fit the average woman. The ratio of the bowed height to bowed length is about 2 to 3 for a pad having comfortable fit with good leak resistance.

As stated above, it is preferred in the pad of the instant invention that the bottom of the pad 40 be generally smooth and ungathered while the upstanding baffles 42 and 44 be generally perpendicular to the bottom of the pad. In a preferred method of forming the pad in order to accomplish this structure, the pad is formed of a heat-shrinkable elastic such as that disclosed in co-pending commonly assigned Ser. No. 606,082, filed May 1, 1984, Matray et al. Other known heat-shrinkable materials such as those in Raychem's U.S. Pat. No. 3,636,917 also may be utilized.

Figure 6:
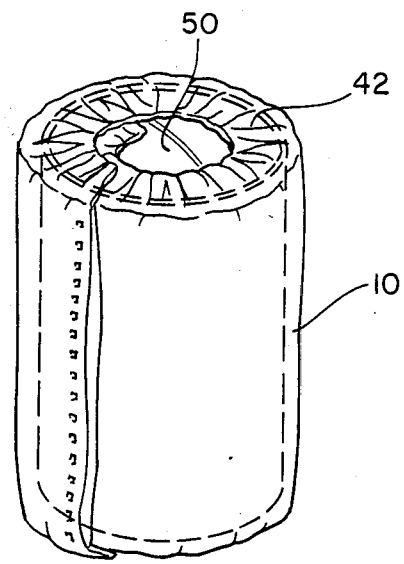
FIG. 6 is a view of a pad cured on a roll.
Figure 7:
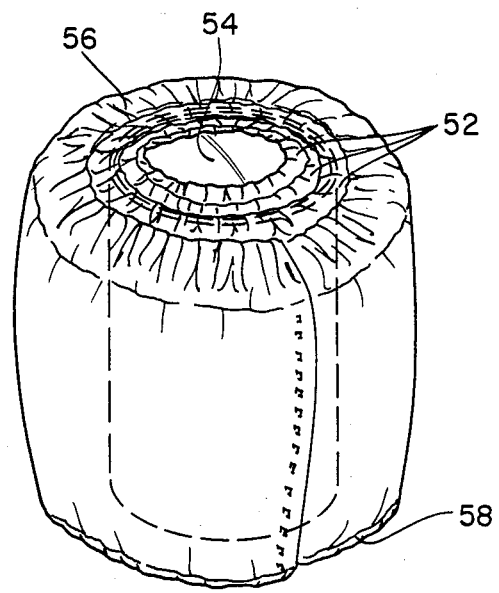
FIG. 7 is a view of a roll of pads that have been cured simultaneously.

FIG. 6 illustrates a preferred forming technique to best obtain the generally smooth and ungathered bottom portion 40 in combination with the raised flaps 44 and 42. As illustrated in FIG. 6, the pad 10 is wrapped onto core 50. After the pad in unshrunken condition is wrapped onto the core, the pad is subjected to heat at the elastic-containing end portions in order to bring about shrinkage and form the flaps 42. As illustrated in FIG. 7, also it is possible within the invention to wrap a series of pads 52 around a core 54 such that a group of the pads may be heated together to shrink the elastic at the ends 56 and 58 of the pad roll. These are the preferred methods as the pads that result have a smoother bottom and more vertical sides than those not shrunk on a form. The means of applying heat to shrink the heat-shrinkable elastic may be any suitable means. Suitable heating means are those such as hot air or microwave heating.

Nevertheless it is possible to form the pads of the invention with stretched elastic which will cause the pad to immediately assume the bowed shape when the stretched elastic is relaxed. Pads formed by this method, as they are not shrunken over a form, have a more rounded bottom than the preferred pads, but nevertheless form a double-baffle system providing comfort to the wearer. It is theorized that with the preferred embodiment the flat bottom is more likely to bend upward against the genital region when it is worn. By bending upward against the genital region, the urine or menstrual flow will contact the pad immediately on being exuded and is more likely to be absorbed prior to spreading or leaking from the edge of the pad.

Figure 8:
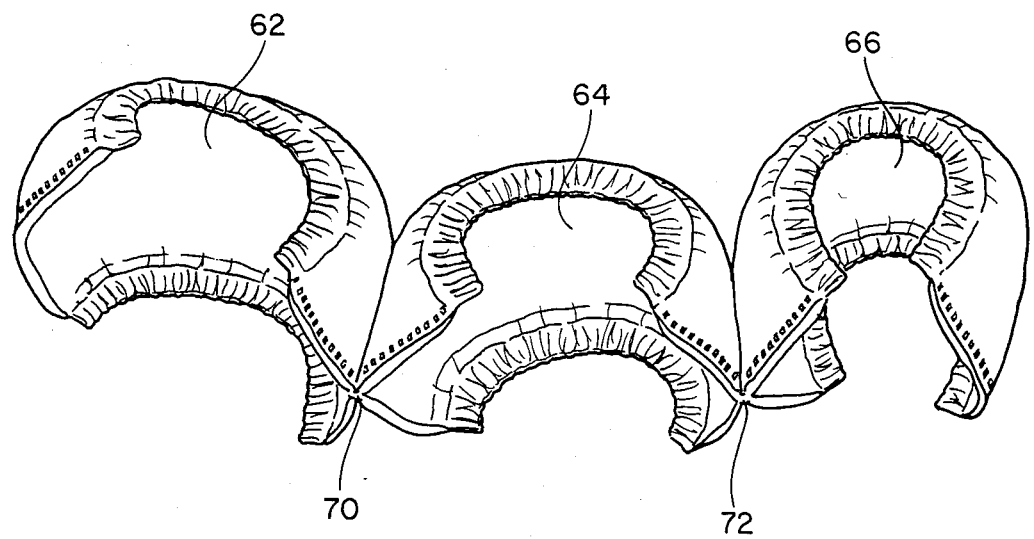
FIG. 8 is a group of pads that are connected.

Illustrated in FIG. 8 is a series of the pads of the invention indicated as pads 62, 64, and 66. The pads are joined by small portions of the impervious backing sheet at 70 and 72. These sheets may be detached prior to being packaged for sale.

Figure 9:
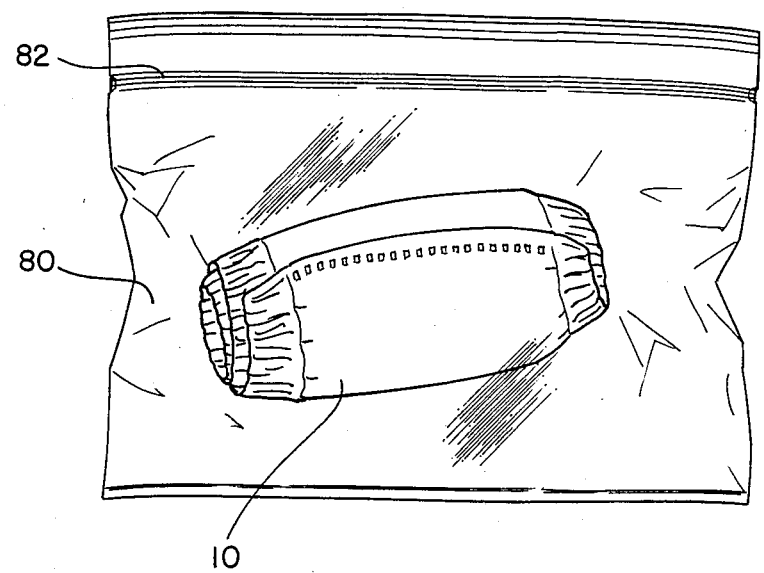
FIG. 9 is a view of a package containing a pad of the invention.

FIG. 9 is an illustration of a packaging system that the pad of the invention is particularly suitable for. As shown in FIG. 9, a pad of the invention 10 is placed within a transparent bag 80 that is sealed by a pressure-sensitive adhesive at 82. The pressure-sensitive adhesive may be replaced by other sealing means such as heat sealing or a zip-lock type seal. The pad 10 may be rolled as shown, thereby taking very little room in the purse or bag of the wearer. Further, the pad may be discreetly disposed of in the bag without the release of odor or liquid if a place for disposal is not available when it is changed. The ability to be rolled without losing overall shape when unrolled is an advantage of this invention that allows the discreet packaging in a bag such as 80. Such discreet packaging is important to incontinent care articles.

The impervious backing sheet 12 is impervious to liquids. It serves to prevent the soiling of the garments of the wearer by preventing the penetration of the moisture. It is possible that the material could be vapor permeable while being liquid-impermeable. The impervious backing sheet may be formed of any suitable plastic film. Typical such films are polyethylene films having a thickness of from 0.0005 to about 0.002 inches. A particularly preferred sheet is a coextruded sheet of spunbonded polyethylene filaments with a sheet of polyethylene. The spunbonded material is placed on the exterior of the garment and is preferred as it is believed to provide added strength as well as providing a better feel in a cloth-like surface and is quieter when worn. Suitable coextruded sheets are that available from Printpak Inc. and include a film such as that marketed as Film No. 97-55508.

The absorbent layer may be selected from any of the known absorbent materials for use in absorbent pads. Typical of such materials are the divellicated wood fibers, polyester fibers, cotton fibers, or other known absorbent fiber materials. A preferred material is the material commonly known as "coform." This material is an air-formed blend of meltblown polypropylene and divellicated wood fibers. A particularly preferred coform has about 70 weight percent wood fiber material and about 30 weight percent polypropylene meltblown material. In an optimum form the coform material may be simultaneously combined with a superabsorbent as it is meltblown. This technique is disclosed in copending and coassigned application, U.S. Ser. No. 60/602,993, filed Apr. 23, 1984, inventors T. McFarland and T. Lang. Such a material is highly absorbent but does not allow release of superabsorbent or present a slimy feel to the wearer.

The body-side permeable web may be any compliant, soft-feeling, nonirritating and permeable material. Typical of such materials are a wide range of materials such as porous foams, apertured plastic films, natural fibers, synthetic fibers such as polyester, polypropylene, or a combination of natural and synthetic fibers. The body-side permeable layer serves to prevent contact of the pubic region of the wearer with the wet absorbent material. A preferred material has been found to be the spunbonded polypropylene liner material such as is known for diaper liner use. Another preferred material is the permeable web material that is formed with a transfer layer integrated to a nonwoven cover as disclosed in U.S. Pat. No. 4,397,644, Mathews et al. The preferred material may be treated with a wetting agent or surfactant to make it hydrophilic. The web also may be bonded to the coform layer. The bonding to the coformed layer is believed to aid in passing of liquids through the permeable member rather than having them run along the surface. It is noted, however, that the dual baffle system of the invention does serve to prevent overflowing of liquids running along the surface of the liner as the upstanding baffle will divert the liquid onto the absorbent surface prior to its passing over the side of the pad.

The pad may be any suitable size that will conform to the genital region of the wearer. While the pad has generally been discussed for use by women, it is also believed suitable for use by men, particularly in the larger sizes or with larger upstanding baffles. Generally, the range of width of the absorbent is between about 2 and about 4 inches. A preferred width absorbent is about 3 inches so as to result in a pad of a width comfortable for most persons.

The height of upstanding baffles 42 and 44 may be any suitable height that will give comfort and low leakage. Generally it is preferred that the baffles have a height between about one-half inch and five-eighths inch for a woman's pad that will be comfortable and provide good leakage protection. The baffle heights for men may be between about one inch and about one and one-half inch in order to provide contact with the periphery of the pubic or genital area while allowing room for the genitals.

The amount of the overlap of the impervious backing sheet 40 in area 22 and 25 over the absorbent 14 to form the lower baffle may be selected to give good protection against leaking around the edges while at the same time not interfering with urine discharge into the pad. A preferred range of overlap of the absorbent by the packing material to form the lower baffle at areas 22 and 25 is a lower baffle of between about one-half inch and one-fourth inch width on each side so as to not interfere with urine discharge into the pad, but still retain the baffling effect for any liquid that is squeezed from the absorbent or has not yet been absorbed by the absorbent.

While the device of the invention finds primary use as an incontinent or catamenial device, it is possible that the device could find utility as a bandage for the elbow, knee or foot.

The device of the invention used as an incontinent or catamenial pad may be worn inside tight-fitting underpants or may be held in place on the underpants by adhesive points 43 and 45 as shown in FIG. 3. Alternatively, one or a series of adhesive strips could be placed on the length of the pad and covered with a peel strip that would be removed prior to the garment being placed inside the underwear. It is preferred that adhesive area be located near the end such as shown in FIG. 3 as the suspension of the device from the ends seems to give better comfort and protection. The device also could be held in place by belt devices that are known in the art for use with menstrual pads.

In describing the present invention, certain embodiments have been used for purposes of illustration; however, other embodiments or modifications within the spirit and scope of the invention will readily occur to those skilled in the art after reading of this disclosure. The invention is accordingly not to be limited to the specific embodiments illustrated, but only in accordance with the appended claims.

I claim:

1. A generally rectangular bowed absorbent pad comprising an impervious backing sheet, an inner generally rectangular absorbent layer and a body-side permeable web wherein said impervious backing extends beyond the long sides of said rectangular absorbent layer and is folded back on each side and adhered to said permeable web, and wherein elastic members in extended condition are adhered within the folds of said impervious sheet, wherein said impervious sheet is adhered to itself in the area of the folds between said elastic members and said absorbent, said bowed pad has a bowed length of between about 6.5 and about 12 inches and a bowed height of between about 2 and about 3.5 inches, wherein a lower baffle is formed where said backing sheet is adhered to said permeable web, wherein when said elastic contracts the folded impervious sheet forms an upstanding baffle that extends between about 0.5 and about 1.5 inches above the absorbent pad and wherein said elastic extends substantially the entire length of said pad.

2. The pad of claim 1 wherein said backing is adhered both to said absorbent and to said permeable web.

3. The pad of claim 1 wherein the pad is trough-like in shape and has a smooth and ungathered bottom.

4. The pad of claim 1 wherein said absorbent comprises coform.

5. The pad of claim 1 wherein said pad has a preferred bowed length of between about 7.5 and 8 inches.

6. The pad of claim 1 wherein the backing is provided with at least one adhesive area for fastening to a wearer's undergarments.

7. The pad of claim 6 wherein adhesive areas are located near the ends of said pad.

8. The pad of claim 1 wherein said absorbent is between about 2 and about 4 inches wide.

9. The pad of claim 1 wherein said baffles extend between about one-half inch and about five-eighths inch above the pad.

10. The pad of claim 1 wherein the folded impervious backing sheet overlaps said absorbent member about one-half to about one-fourth inch on each side of said absorbent member forming the lower baffles.

11. The pad of claim 1 wherein a lower baffle is formed by folding said impervious backing sheet and adhering said sheet to said permeable web and said absorbent layer such that said sheet covers the outer about one-half to one-fourth inch of absorbent on each side of said pad.

* * * * *